(12) United States Patent
Thilly et al.

(10) Patent No.: US 7,946,437 B2
(45) Date of Patent: May 24, 2011

(54) CLOSURE SYSTEM FOR A VIAL, VIAL, METHOD OF CLOSING AND FILLING A VIAL AND STAND FOR A VIAL

(75) Inventors: Jacques Thilly, Rixensart (BE); Christian Vandecasserie, Rixensart (BE)

(73) Assignee: Aseptic Technologies S.A. (BG)

( * ) Notice: Subject to any disclaimer, the term of this patent is extended or adjusted under 35 U.S.C. 154(b) by 1434 days.

(21) Appl. No.: 10/524,886

(22) PCT Filed: Aug. 15, 2003

(86) PCT No.: PCT/EP03/09151
§ 371 (c)(1), (2), (4) Date: Dec. 1, 2005

(87) PCT Pub. No.: WO2004/018317
PCT Pub. Date: Mar. 4, 2004

(65) Prior Publication Data
US 2006/0091098 A1     May 4, 2006

(30) Foreign Application Priority Data

Aug. 16, 2002 (GB) .................. 0219152.6
Feb. 25, 2003 (GB) .................. 0304268.6

(51) Int. Cl.
*B65D 51/20* (2006.01)
*B65D 41/46* (2006.01)
(52) U.S. Cl. ............... 215/249; 220/254.3; 604/415
(58) Field of Classification Search ........... 215/247, 215/249, 253, 355; 220/254.3, 257.1; 604/415
See application file for complete search history.

(56) References Cited

U.S. PATENT DOCUMENTS

| | | | | |
|---|---|---|---|---|
| 2,783,908 A * | 3/1957 | Winfield | ............... | 215/247 |
| 4,243,150 A * | 1/1981 | Gunne et al. | ............... | 215/247 |
| 4,275,511 A | 6/1981 | Parkinson et al. | | |
| 5,000,331 A | 3/1991 | Conlon et al. | ............... | 215/100 |
| 5,219,083 A * | 6/1993 | Liebert et al. | ............... | 215/247 |
| 5,447,247 A * | 9/1995 | Derksen | ............... | 215/247 |
| 5,699,923 A * | 12/1997 | Burns | ............... | 215/247 |
| 5,718,348 A | 2/1998 | Manera | ............... | 215/249 |
| 6,068,150 A | 5/2000 | Mitchell et al. | ............... | 215/247 |
| 6,378,714 B1 * | 4/2002 | Jansen et al. | ............... | 215/249 |
| 6,604,561 B2 * | 8/2003 | Py | ............... | 141/329 |
| 6,695,829 B2 | 2/2004 | Hellstrom et al. | | |
| 6,868,978 B2 * | 3/2005 | Amschlinger et al. | ........ | 215/249 |

(Continued)

FOREIGN PATENT DOCUMENTS

DE         12 28 028         11/1966

(Continued)

OTHER PUBLICATIONS

Office action from the Patent Office of the Russian Federation in Application No. 2007115540/06(016882), which is a National Stage filing from PCT/EP2005/011623 by Thilly, 3 pp. (Jun. 11, 2009).

*Primary Examiner* — Gary L. Welch
*Assistant Examiner* — James N Smalley
(74) *Attorney, Agent, or Firm* — Klarquist Sparkman, LLP

(57) ABSTRACT

A closure system for a pharmaceutical vial, comprising an elastomer closure part, a clamp part which holds the closure part in engagement with the mouth of the vial, and a cover part which engages with the clamp part. The interior of the closure part is profiled to minimize retention of residual liquid therein.

16 Claims, 4 Drawing Sheets

U.S. PATENT DOCUMENTS

2002/0023409 A1    2/2002    Py .................................. 53/426

FOREIGN PATENT DOCUMENTS

| DE | 18 11 304 | 6/1970 |
| DE | 90 05 326 | 8/1990 |
| EP | 0 564 037 | 10/1993 |
| FR | 2 516 480 | 5/1983 |
| FR | 2 598 137 | 11/1987 |
| WO | WO 0160699 A2 * | 8/2001 |

* cited by examiner

CLOSURE SYSTEM FOR A VIAL, VIAL, METHOD OF CLOSING AND FILLING A VIAL AND STAND FOR A VIAL

This application is a 371 of International Application No. PCT/EP03/009151, filed 15 Aug. 2003.

This invention relates to a novel device, being a closure system for vials, particularly for pharmaceutical vials, for the sterile containment of drug substance or vaccine products therein.

Drug substance and vaccine products are frequently provided in vials which are closed with an elastomer closure part through which a hollow needle can be passed, puncturing the closure part, and via which the drug substance or vaccine product may be extracted for use, optionally after reconstitution by an aqueous medium introduced into the vial via the needle. Normally such a vial has a mouth opening bounded by a flange-shaped rim, and the closure part is held in a closing relationship with the mouth opening by a flexible metal clamp part which surrounds the perimeter of the closure part and holds it tightly against the rim. Often a central area of the closure part may be punctured by the needle, and the clamp part has a removable central part, which prior to use covers this central area of the closure part, and which can be removed immediately before use. Often this central part is connected to peripheral parts of the clamp part by thin frangible links, enabling the central part to be initially connected to the peripheral parts and detached prior to use, giving tamper evidence. A problem with this known device is that it is difficult to achieve a sterile seal between the central part and closure part, so the user has to "santise" the central area of the closure part immediately prior to use, e.g. using an alcohol wipe. FR-A-2 516 480 discloses a vial with a clamp part over its elastomer closure, and with a peel-off cover over, a central aperture in the clamp part.

It is also known, e.g. from US-A-2002/0023409, to provide a pharmaceutical vial having a closure part made of thermoplastic material. Such a vial can be filled using a hollow needle passed through the closure part, the needle is then withdrawn, and the small residual puncture hole may then be sealed by heat sealing, e.g. using a focussed laser beam. It is an object of this invention to improve the vial disclosed therein.

It is also an object of this invention to provide an improved vial closure system having ease of construction, assembly and reduced loss of contents.

It is an object of the present invention to provide a vial closure system which in part at least overcomes the above-mentioned problems of known closure systems, and is particularly suited to vial closures which can be heat-sealed after filling using a hollow needle, as described above. Other objects and advantages of the present invention will be apparent from the following description.

According to this invention, a closure system is provided for a vial of the type having an upwardly-facing mouth opening bounded by a rim, the closure system comprising:

an elastomer closure part shaped to sealingly engage with the mouth opening, having a lower surface facing the interior of the vial and an opposite upper surface facing away from the vial, and capable of being punctured by a needle, a clamp part able to engage with the vial, particularly with the rim of the mouth opening, and able to bear upon the upper surface of the closure part to hold the closure part in a closing relationship with the mouth opening, the clamp part having an aperture therein through which a region of the upper surface of the closure part is exposed when the clamp part is engaged with the vial, a cover part, engageable with the clamp part and/or the vial to cover the said region of the closure part when so engaged.

Preferably a lower surface of the cover part facing the upper surface of the closure part when so engaged has a sealing ridge projecting therefrom to a sealing edge that follows a closed perimeter, so that when the cover part is engaged with the clamp part and/or the vial the sealing edge engages with the closure part to form an enclosure with the closure part, and at least that part of the cover part which includes the sealing ridge is removable from engagement with the clamp part and/or the vial.

The terms "upward", "upper", "lower" etc. and derived directional terms such as "vertical" are based on the normal configuration of a vial in a vertical orientation with the mouth uppermost and its base downward.

The vial is preferably of the type having a neck immediately downward of the mouth opening, and having a rim in the form of a flange having upper and lower surfaces extending transverse to, preferably perpendicular to, the upper-lower axis. Such vials are well known in the pharmaceutical industry. Suitably the upper surface of the flange may be bounded by a peripheral upwardly-extending kerb edge. Such a kerb edge can help to seat and retain the elastomer closure part on the flange. Suitably the upper surface of the flange may have an upwardly extending sealing ridge to engage against a downward facing surface of the closure part to improve sealing between the closure part and the flange.

The vial may be made of glass, but preferably the vial is made of a hard plastic material accepted for use in the pharmaceutical industry. A suitable type of polymer is a cycloelefin copolymer ("COC"), a blend thereof or a blend thereof with another polymer. Examples of such COC polymers are for example disclosed in U.S. Pat. No. 5,723,189, EP-A-0436372 and EP-A-0556034 among others. A suitable hard plastic material accepted for use in the pharmaceutical industry is the cyclolefin copolymer "Topas" made by Celanese Corporation. For example the known COC polymers Topas 8007 or Topas 6015 may be used, available from for example Ticona GmbH (DE). Conditions for injection moulding this polymer to make vials therefrom are known in the art.

The closure part preferably has a downwardly extending plug part which fits into the mouth opening of the vial, and an outwardly extending peripheral flange part, a downward facing surface of which can engage with the upward facing surface of a rim of the vial mouth opening when this is in the form of a flange. Suitably the plug part has an outer perimeter e.g. of its peripheral flange which fits conformingly within the kerb of the flange. Upwardly of such a flange part the closure part may be flat but is preferably upwardly convex, e.g. domed or of a (frustro) conical shape. The plug part is suitably of a hollow cylindrical shape with an upper end of the hollow cylindrical interior extending into this upper domed or conical part, e.g. such that the overall internal shape of the closure part is a bell- or dome-shape or a cylinder with an upper closed end of a domed or concave frustro-conical shape.

Preferably at least the upper surface of the closure part adjacent to the said region, preferably an upper part, preferably the whole of the closure part is made of a thermoplastic elastomer material, so that a puncture hole formed as a result of filling the vial using a hollow needle may be sealed by thermal sealing, e.g. using a focused light beam such as a laser as described in US-A-2002.0023409. A suitable thermoplastic elastomer may be based on styrenic block copolymer thermoplastic elastomers as commonly used for vial closures. A suitable thermoplastic elastomer material is a 50:50 w:w blend of the polymers "Engage" supplied by Dupont-Dow, and "Dynaflex" formerly known as "Kraton" as supplied by Shell but now available from GLS (USA) who supply this blend, and including a dye, e.g. grey in colour, to enhance absorption of laser light so that the thermoplastic elastomer material may be heated using laser light. Under irradiation from a focussed 980 nm laser this thermoplastic elastomer material easily fuses at ca. 180° C. and sets on cooling.

The clamp part is preferably made of a mouldable plastics material, and is able to engage with the vial, preferably being engageable with the above-mentioned flange around the rim of the mouth opening of the vial, for example by a snap-fit engagement underneath a downwardly facing surface of such a flange part. The clamp part preferably comprises an upper wall part having the aperture therein, preferably a central aperture, with peripheral skirt walls extending downwardly therefrom and having snap-fit engagement parts thereon to engage with the vial, e.g. with the said flange. Preferably the clamp part is made of a resilient plastics material such as a polypropylene, polyamide etc. and is dimensioned so that when so engaged with the vial the clamp part can resiliently exert a compressive force upon the vial, e.g. the flange around the rim of the mouth opening and the closure part to compress them together and so to enhance sealing between the closure part and the vial.

A vial in which an elastomer material closure part is held in a closing relationship with the vial by means of a resilient plastics material clamp part is believed to be novel and is consequently a further part of this invention.

Therefore the present invention further provides a closure system for a vial of the type having an upwardly-facing mouth opening bounded by a rim, the closure system comprising:

an elastomer closure part shaped to sealingly engage with the mouth opening, having a lower surface facing the interior of the vial and an opposite upper surface facing away from the vial, and capable of being punctured by a needle, a clamp part able to engage with the vial, particularly with the rim of the mouth opening, and able to bear upon the upper surface of the closure part to hold the closure part in a closing relationship with the mouth opening, the clamp part having an aperture therein through which a region of the upper surface of the closure part is exposed when the clamp part is engaged with the vial, and wherein the clamp part is made of a resilient plastics material and is dimensioned so that when so engaged with the vial the clamp part can resiliently exert a compressive force upon the vial and the closure part to compress them together and so to enhance sealing between the closure part and the vial.

Preferred features of this aspect of the invention are as discussed above.

If the closure part has the above mentioned upwardly convex shape, then preferably the upper wall of the clamp part and the upwardly convex part of the closure part are externally profiled such that the upwardly convex part of the closure part bulges above the adjacent upper surface of the upper wall when the clamp part and closure part are in place. This bulging of the closure part above the upper wall part encourages sealing between the closure part and the cover part when in place. The lower surface of the clamp part where this is in contact with the closure part may be profiled to match the shape of the upper surface of the closure part so that the clamp part and closure part mate together. Preferably the upper surface of the clamp part and the upwardly convex part of the closure part are profiled to form a smooth convex shape. Such a smooth convex shape minimises disturbance to a downward laminar flow of air directed over the combination of vial, closure and clamp and so facilitates the processing of the combination in a sterile environment.

The cover part is preferably engageable with the clamp part. For example the cover part may be engageable by snap-fit means with the upper wall, or skirt wall of the clamp part, or the junction region between the upper wall and skirt wall. For example the cover part may comprise a cap having an upper wall and a peripheral skirt wall, and the skirt wall of such a cap may have a snap-fit engagement part, e.g. adjacent its lower extremity, to engage with the clamp part. Such snap-fit means may comprise a ridge on the cover part and a corresponding groove on the clamp part, or vice versa. Other snap-fit means will be apparent to those skilled in the art and may be used.

The cover part covers the region of the closure part which is exposed through the aperture in the clamp part. The cover part preferably at least partly closes the aperture, preferably a centrally positioned aperture in the clamp part to thereby cover the above-mentioned region of the closure part, preferably a central region of the closure part. The sealing ridge may be located on the cover part and extend downwardly from the lower surface of the upper wall of the cover part which is adjacent to and above the closure part when the cover part is engaged with the clamp part, and may be an integrally made part of the cover part. Alternatively the sealing ridge may be located on the closure part and extend upwardly from the upper surface of the closure part which is exposed through the aperture and may be an integrally made part of the closure part, in which case the sealing ridge extends downwardly from the lower. The sealing ridge has a sealing edge which preferably has a generally triangular section as cut parallel to the up-down direction, so that the sealing edge comprises the apex of the triangle. The sealing edge preferably follows a ring-shaped, e.g. circular, oval or polygonal closed perimeter as viewed looking upwardly toward the lower surface of the upper wall of the cover part.

The part of the cover part which includes the sealing ridge is preferably made removable from the clamp part and/or vial as follows. Preferably the upper wall has a segment, e.g. a pie-slice segment of a generally circular upper wall, linked to the remainder of the upper wall and/or skirt wall by one or more thin, frangible link, which may be integrally made with the cover part and its removable part, which can easily be severed to allow the segment to be sufficiently (partly or wholly) detached from the remainder of the cover part to allow access to the region of the closure part exposed through the aperture.

Suitably the cover part may be made by injection moulding of a plastics material, suitably of the same plastics material as the clamp part.

The present invention further provides a vial when fitted with a closure system as described herein.

In a further aspect of this invention it has also been found that the internal profile of the plug part of the closure part can be important in ensuring that minimal liquid content remains trapped in the vial when liquid content is removed therefrom using a needle.

Generally the plug part of a vial closure, e.g. as described above is generally hollow tubular, and has an outward-facing vial neck-contacting surface which engages with the interior surface of the vial neck, typically being a cylindrically-shaped outer surface which when the closure is in place is against the cylindrical interior surface of the vial neck, and an interior-facing surface which is exposed to the interior of the vial, and which merges with the neck-contacting surface at the point where the interior-facing surface meets the interior surface of the vial neck. In known plug parts of the state of the art, for example as shown in EP-A-0956849 FIG. 4 and EP-A-0794129 when the closure is in place the interior-facing surface of the plug part encloses an angle of 90° or less with the interior surface of the vial neck immediately below the plug part. This results in the problem that due to capillary action and/or surface tension liquid content becomes trapped in this acute angle and cannot easily be removed using a needle. In a small vial a significant proportion of the content can become trapped in this way.

Therefore according to this further aspect of the invention a vial closure is provided having a plug part which has an outward-facing neck-contacting surface which engages with the interior surface of the vial neck when the closure is in place against the cylindrical interior surface of the vial neck, and an interior-facing surface which is exposed to the interior of the vial and which when the closure is in place encloses an angle of greater than 90° with the interior surface of the vial neck immediately below the plug part.

Preferably this angle is in the range 120-160°, for example ca. 135°+/−10°.

This angle may be achieved by the outward-facing neck-contacting surface of the plug part being generally cylindrical, at least adjacent the lower end of the plug part, and by the interior-facing surface and the outward-facing neck-contacting surface forming an edge enclosing an angle less than 90° between them. Preferably this angle is in the range 30-60°, for example ca. 45°+/−10°. It will of course be appreciated that in practice when making the plug part of an elastomer material using for example injection moulding it may be necessary for such an edge to deviate from a perfect knife edge, for example having a small radius of curvature, e.g. of 0.5 mm or less, or a small flat edge.

When the interior-facing surface encloses an angle of greater than 90° with the interior surface of the vial neck immediately below the plug part in this aspect of the invention it is found that this minimises the tendency of surface tension and capillary effects to cause residual liquid content in the vial to become trapped between the closure and the interior surface of the vial.

The present invention also provides a method of closing a vial, wherein:

a vial is provided being of the type having an upwardly-facing mouth opening bounded by a rim in the form of a flange having upper and lower surfaces extending transverse to its upper-lower axis.

an elastomer closure part shaped to sealingly engage with the mouth opening, having a lower surface to face the interior of the vial and an opposite upper surface to face away from the vial, and capable of being punctured by a needle is inserted into the mouth opening of the vial, a clamp part is provided able to engage with the flange around the rim of the mouth opening of the vial by a resilient snap-fit engagement of a snap fit part of the clamp part underneath a downwardly facing surface of such a flange part, and able to bear upon the upper surface of the closure part to hold the closure part in a closing relationship with the mouth opening, and the clamp part is engaged with the assembly of vial and closure part by said snap-fit engagement.

Preferred features of the vial, closure part and clamp part are as described above.

Preferably in this method, subsequent to the engagement of the clamp part with the assembly of vial and closure, a cover part is provided, engageable with the clamp part and/or the vial to cover the closure part when so engaged, a lower surface of the cover part to face the upper surface of the closure part when so engaged, and the cover part is engaged with the clamp part.

Preferred features of the clamp part are as described above.

The present invention also provides a method of filling a vial comprising:

providing an assembly of an empty vial having a closure part and clamp part thereon;

inserting a filling needle downwardly through the upper wall of the closure part;

injecting a liquid medicament through the filling needle to fill the vial to a suitable extent;

withdrawing the needle to leave a residual puncture hole;

engaging a cover part with the clamp part.

Preferably prior to engaging the cover part a laser beam or other source of heat is directed at that part of the upper surface of the closure part where the puncture has occurred to melt the elastomer material in the immediate locality of the puncture, and to thereby seal the residual puncture hole.

The above-mentioned assembly may be supplied from a separate source, so as a further aspect this invention provides:

a pharmaceutical vial having a mouth opening closed by an elastomer closure part shaped to sealingly engage with the mouth opening and having a lower surface facing the interior of the vial and an opposite upper surface facing away from the vial, and capable of being punctured by a needle, a clamp part engaged with the rim of the mouth opening, and able to bear upon the upper surface of the closure part to hold the closure part in a closing relationship with the mouth opening, the clamp part having an aperture therein through which a region of the upper surface of the closure part is exposed when the clamp part is engaged with the vial, the clamp part and/or vial being engageable with an at least partly removable cover part able to cover the said region of the closure part and being able to form an enclosure with the closure part.

In such a method, the automatic handling of a vial, e.g. a vial fitted with a closure system, or with the closure part and clamp part of a closure system as described herein, on a conveyor system by means of which the vial may be transported to one or more station where an operation such as filling using a needle or laser-sealing the residual puncture site is facilitated by a stand for the vial, and a vial construction which comprises a further aspect of this invention.

According to this further aspect of the invention a stand for a vial is provided comprising a ring-shaped body having an inner perimeter such that the base of a vial may fit therein and be retained therein, the stand having an outer perimeter which extends, in a direction perpendicular to the mouth-base axis direction of a vial retained therein, beyond the outer diameter of the vial body, and has an upward-facing surface.

Suitably the outer perimeter of the stand extends radially to substantially the same distance as the radially outermost extent of a part of the vial or its combination with the clamp part or cover part above the stand. When combined with such a stand and a clamp part of similar outer radius this facilitates rolling the vial, e.g. for labeling, and also helps plural vials to stack together stable in an upright alignment.

Such a stand preferably has upward facing and lower surfaces which are substantially flat and parallel. Such a stand is useful in facilitating handling machinery to hold the vial by the stand, e.g. by bearing upon the upward facing surface of the stand and pressing the stand downwardly e.g. against part of a conveyor. If the vial is being handled in a sterile environment provided by a downward laminar flow of air this enables the vial to be held by its stand at a part downstream of the closure part, so reducing the risk of contamination being carried from the handling machinery to the vial closure. Also if the vial is used in the above-described method of filling a vial, in the step of withdrawing the needle, the upward facing surface facilitates restraining of the vial against the upward withdrawing force of the needle by abutment of the upward facing surface against an abutment, e.g. part of the handling machinery.

The invention also provides a combination of a vial having a base which can engage with the inner perimeter of such a ring-shaped stand, and such a stand.

For example such a vial may have a base having an upper surface forming the bottom inner surface of the vial, and a lower surface from which extends downwardly an engagement part able to engage with the inner perimeter of such a stand, e.g. in a male-female plug and socket engagement between the engagement part and the inner perimeter of the stand.

If the vial is to be transported on a conveyor system, then to maintain a sterile environment it is normal to direct a downward flow of purified air over the conveyor and vials thereon. Such a stand provides the advantage that it can easily be gripped by gripping means on a conveyor, enabling the vial to be held such that the closure is uppermost and therefore upstream in the flow of air, minimising the risk of contamination of the closure with micro-organisms.

The invention will now be illustrated by way of example only with reference to the following drawings.

Figure 1:
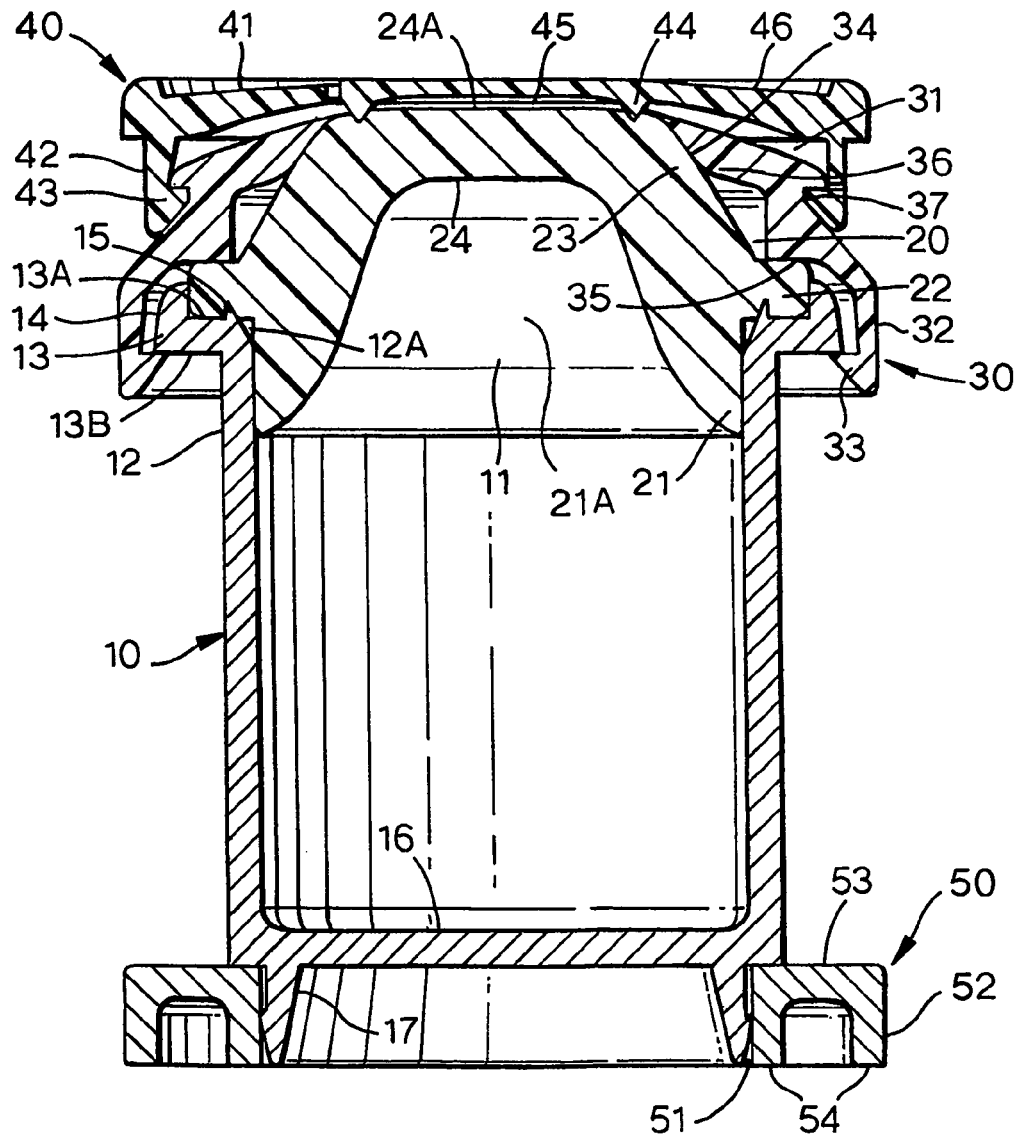
FIG. 1 shows a longitudinal section of a vial and vial closure system according to this invention cut along an up-down plane.

10 vial
11 mouth opening
12 neck, 12A upper inner edge of the neck
13 rim, 13A upper surface, 13B lower surface
14 peripheral kerb 14
15 sealing ridge
16 vial base
17 integral engagement part
20 closure part
21 plug part, 21A interior of the plug part
22 outwardly extending flange
23 upper part of the closure part
24 upper wall, 24A central region
30 clamp part
31 upper wall
32 skirt wall
33 snap fit engagement parts
34 upper downward facing surface
35 lower downward facing surface
36 central circular aperture
37 groove
40 cover part
41 upper wall.
42 peripheral skirt wall
43 snap fit engagement parts
44 sealing ridge
45 sealed enclosure
46 removable segment of the upper wall and skirt wall of the cover part
47 thin severable links
50 ring-shaped stand
51 inner perimeter
52 outer perimeter
53 upper surface
54 lower surface Referring to FIG. 1 a vial 10 is shown being of generally cylindrical shape. At its upper end as shown the vial has a mouth opening 11, with a neck 12 immediately below. Vial 10 is shown in its conventional orientation with its mouth uppermost and its base downwards. Larger capacity vials 10 may have a wider body section below their neck 12, as is well known in the art. The mouth opening 11 is surrounded by an outwardly extending rim 13 in the form of a flange having an upper surface 13A and a lower surface 13B. The upper surface 13A of flange 13 is bounded by a peripheral kerb 14. From upper surface 13A of flange 13 a sealing ridge 15 extends upwardly being of generally triangular section as cut along the vertical axis and of circular ring shape concentric with the cylindrical vial 10 in plan. The upper inner edge 12A of the neck 12 in the region of the junction between neck 12 and flange 13 is of a conical profile flaring upwardly, to guide the insertion of the plug part 21 (to be described) of the closure part 20.

Inserted into mouth opening 11 and extending some way down neck 12 is the plug part 21 of a closure part 20 made integrally of a thermoplastic elastomer material. The plug part 21 is a tight fit into the neck 12 to thereby form a tight seal between the closure part and neck. The closure part 20 has an outwardly extending flange 22, of shape and dimensions such that flange 22 fits comfortably within kerb 14. The flange 22 has an upper surface and a lower surface. When the closure 20 is in position as shown in FIG. 1 the lower surface of flange 22 fits against the upper surface 13A of flange 13 and the sealing ridge 15 compresses and deforms the elastomer material of the lower surface of flange 22, contributing to a good seal between surfaces 13A and the lower surface of flange 22.

The plug part 21 is of generally cylindrical shape and has a hollow generally bell-shaped interior 21A. The upper part 23 of the closure part 20, centrally inward of flange 22 is upwardly convex, being of a frusto-conical shape having a flat upper surface. The upper part of the interior 21A of the plug part generally follows the upward convex shape of the upper part 23. The upper end of the cylindrical interior 21A is closed by an upper wall 24 which is thin enough to be punctured by a hollow needle (not shown) by which the vial 10 can be filled whilst the closure part 20 is in place.

A clamp part 30 holds the closure part 20 in place against the flange 13. The clamp part 30 comprises an upper wall 31 generally circular in plan, from the periphery of which downwardly extends a skirt wall 32. At the lower extremity of the skirt wall 32 is a snap fit engagement part 33, being a wedge shaped inwardly extending lip, part lip or teeth, which can engage under the lower surface 13B of flange 13 to hold the clamp part 30 in place on the assembly of vial 10 and closure part 20. The clamp part 30 is made of a resilient plastics material to facilitate this. The clamp part 30 has two regions of downward facing surfaces, being an upper downward facing surface 34 and a lower downward facing surface 35 which bear respectively upon the upper surface of the upper wall 24 of the closure part 20 and upon the upper surface of the flange 22 to hold closure part 20 in place against flange 22.

In the upper wall 31 of the clamp part 30 is a central circular aperture 36, through which bulges the central convex part of the upper part 23 of closure part 20 so that a central region 24A of the upper wall 24 is exposed through the aperture 36. The upper surface of the closure part 20 is profiled so that the upper part 23 of closure part 20 projects bulges upwardly through the aperture 36. The inner perimeter of the aperture 36, adjacent to the upper downward facing surface 24, is also shaped to correspond with the outer profile of the upper part 23 of the closure part 20 so that the closure part 20 and the clamp part 30 mate smoothly.

It is seen that the lower surface of the clamp part 30 where this is in conract with the upper surface of the closure part 20 is profiled to match the shape of the upper surface of the closure part 20 so that the clamp part 30 and closure part 20 mate together. It is also seen most clearly from FIG. 6 that the upper surface of the clamp part 30 and the upwardly convex part of the closure part 20 are profiled to form a smooth convex shape.

Around the periphery of the upper wall 31 of the clamp part 30 is a groove 37 with which the cover part 40 engages.

The cover part 40 is in the form of a cap comprising an upper wall 41, with a peripheral skirt wall 42, at the lower extremity of which is a snap fit engagement part 43 being an inwardly directed wedge shaped lip, part lip or teeth, which can engage with the groove 37 on clamp part 30 to retain cover part 40 securely in place on clamp part 30. The cover part 40 is made of a resilient plastic material to facilitate this.

A lower surface of the upper wall 41 has a sealing ridge 44 extending downwardly therefrom. As seen looking upwards toward the lower surface this ridge 44 has a circular ring-shaped plan and is of a triangular section so that it terminates in a lower knife edge sealing edge. As the cover part 40 is held in contact with the clamp part 30 by the snap-fit parts 43, 37 the resilience of the material of the cover part 40 forces the cover part 40 against the central region 24A of the upper part 23 of the closure 20, and the ridge 44 engages with and compressibly deforms the elastomer of the central region 24A to thereby form a seal with the region 24A. A sealed enclosure 45 is thereby formed between the cover part 40 and the closure part 20. The seal between the ridge 44 and the region 24A is sufficient that contaminants such as microorganisms, virus particles etc cannot pass the seal, so the enclosure 45 can remain sterile.

The vial/closure combination 10, 20, 30 shown in FIGS. 1 and 2 may be assembled as follows. Firstly the vial 10 and closure part 20 are provided, preferably in a sterile state, although the combination of vial 10 and closure part 20 may be sterilised after assembly e.g. by radiation. The plug part 21 of closure part 20 is then inserted downwardly into the neck 11 of the vial 20 until the lower surface of flange 22 of the closure part 20 abuts against the upper surface of the flange 13 around the vial mouth, sitting within kerb 14, the conical taper 12A assisting alignment and entry of the plug part 20 into the neck 11. The clamp part 30 is now pressed downwardly over the closure part 20 so that skirt wall 32 descends around the kerb 14 and the snap fit part 33 engages under the flange 13 to hold the closure part 20 securely in place.

Figure 6:
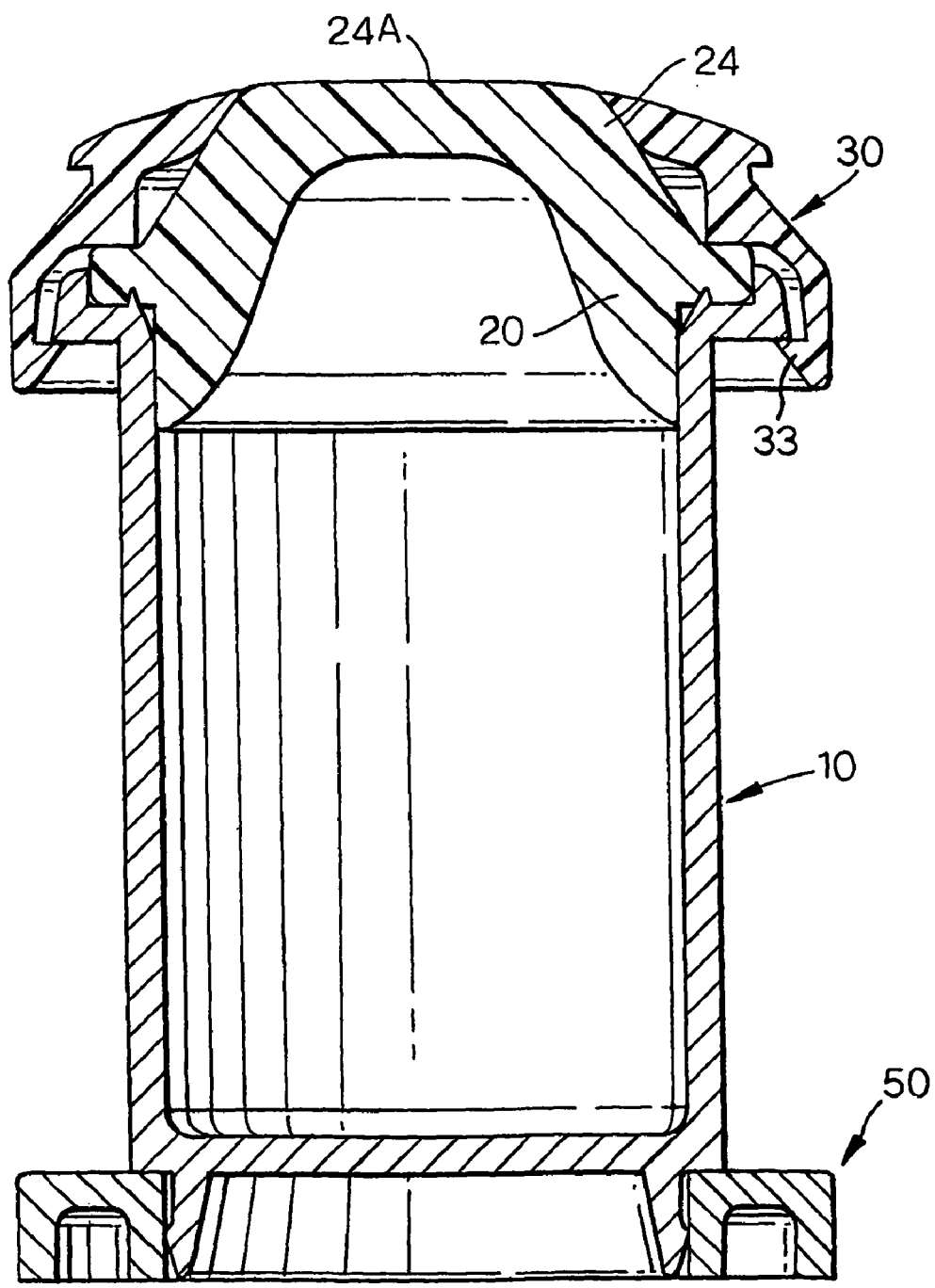
FIG. 6 shows a longitudinal section of a partly assembled vial and closure system of this invention.

The vial 10 and closure system 20, 30, 40 may then be used as follows. An assembly of an empty vial 10, closure part 20 and clamp part 30 is provided as shown in FIG. 6. This assembly may be sterilised by appropriate generally known methods either before (i.e. as separate parts) or after assembly. In a sterile environment such as a flow of sterile air, a filling needle (not shown) may then be inserted downwardly through the upper wall 24 of the closure part 20, and a liquid medicament injected therethrough to fill the vial 10 to a suitable extent. Known filling needles suitable for this purpose may also have an air exit channel to release displaced air from the interior of vial 10. When the vial 10 has been filled in this manner the needle is withdrawn. The vial may be held down against this withdrawing force by an abutment against the upper surface 53 of stand 50. The elastomer material of the wall 24 closes around the residual puncture hole (not shown) in closure part 20, and whilst still in the sterile environment a laser beam or other source of heat is directed at that part of the upper surface of the wall 24 where the puncture has occurred to melt the elastomer material in the immediate locality of the puncture, and to thereby seal the residual puncture hole. Then, still in the sterile environment, the cover part 40 may be engaged with the clamp part as shown in FIG. 1.

Immediately prior to use of the medicament the segment 46 is lifted as described above, and an injection needle attached to a syringe (not shown) may be inserted through the central region 24A, in the normal manner of using a vial closed with an elastomer closure.

Because the central region 24A has been maintained in the sterile enclosure 45 until the segment 46 is lifted, there is no need for the user to give the region of the closure part 20 to be punctured, i.e. the region 24A, a wipe with a sanitising agent as would be necessary with prior art vial closure systems.

Figure 2:
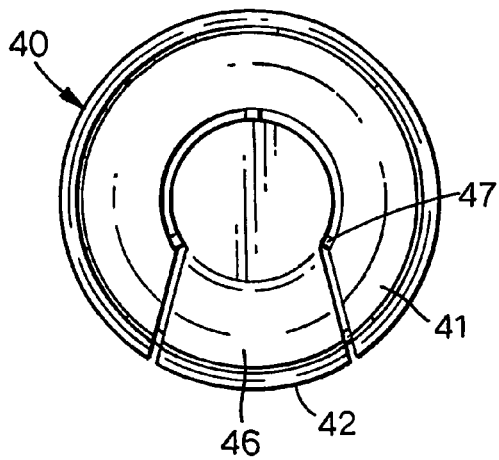
FIG. 2 shows a cover part of a closure system according to this invention viewed in various orientations.
Figure 2:
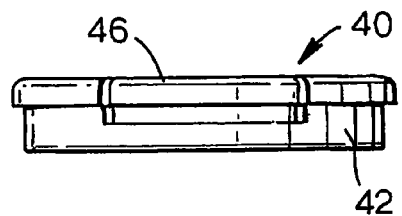
Figure 2:
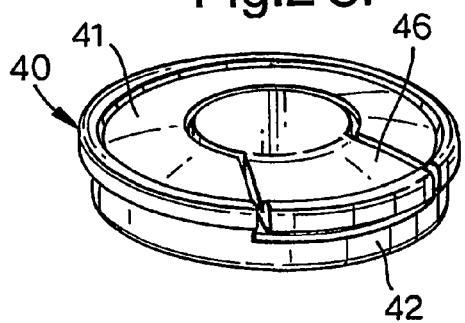
Figure 2:
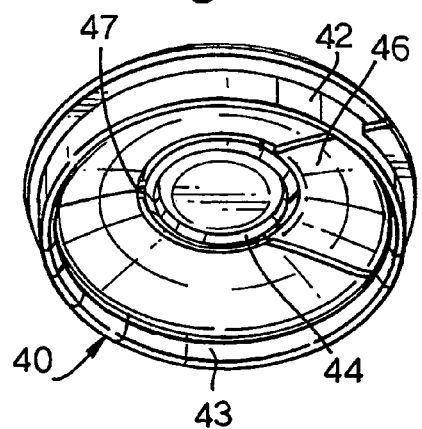
Figure 2:
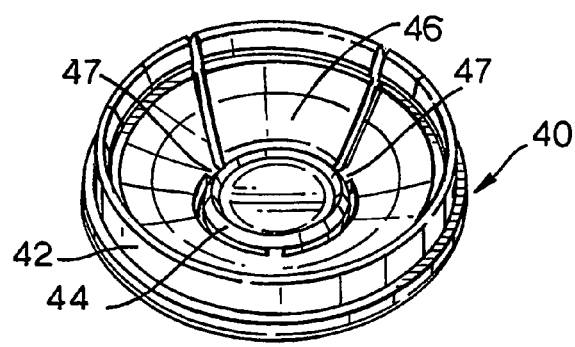
Figure 3:
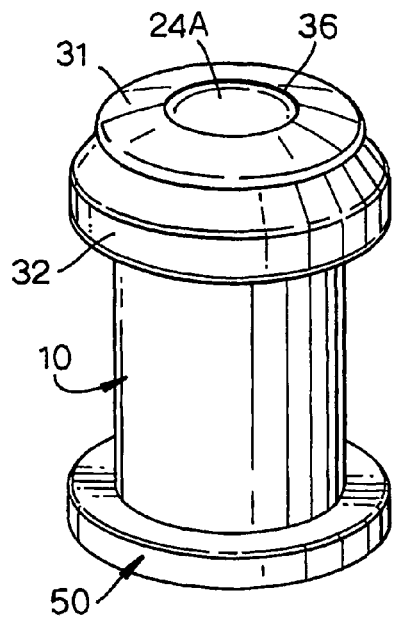
FIG. 3 shows a perspective view of a vial having a closure part and a clamp part in place.
Figure 4:
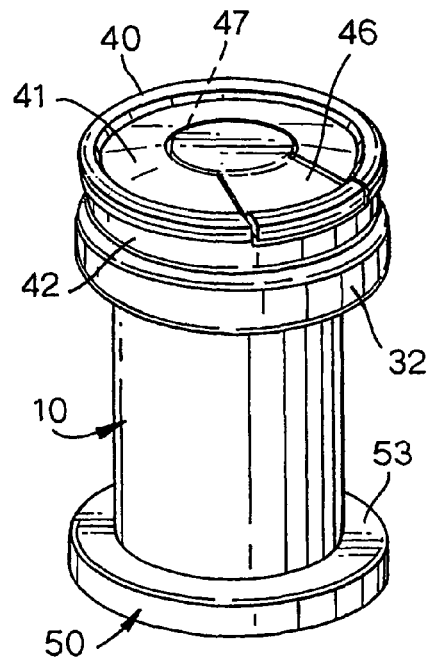
FIG. 4 shows a perspective view of the vial plus closure part and clamp part as shown in FIG. 3, with a cover part also in place.
Figure 5:
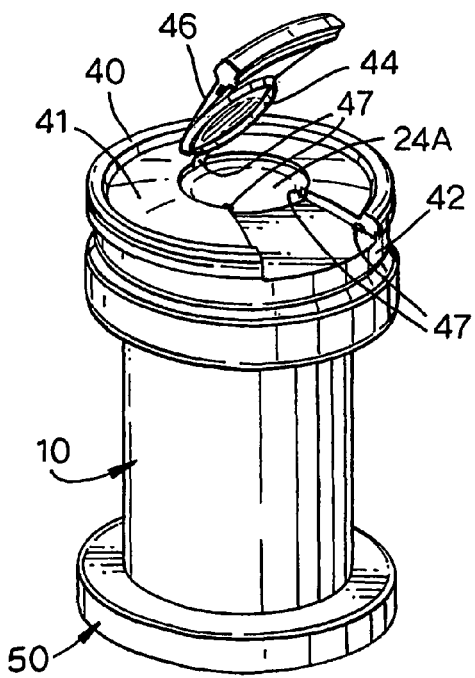
FIG. 5 shows the vial plus closure part, clamp part and cover part of FIG. 4, with the cover part partly removed.

FIGS. 2A-2E respectively show a plan view, a side view looking in the upward direction of FIG. 2A, and three perspective views of the cover part 40. As seen more clearly in FIGS. 2, 3 and 4, whereas the lower part of the skirt wall 42 and its lip 43 extend in a continuous ring, a part 46 of the upper wall 41 of the cover part 40, including that part of the upper wall 41 which has the sealing ridge 44 on its lower surface, is made as a segment which is connected to the remainder of the cover part 40 by thin severable links 47, being integrally made bridges of plastics material. The peripheral edge of this segment 46 may be lifted by a user as shown to thereby break the bridges 47, and to lift the segment 46 from the closure part 20. This breaks the seal between the ridge 44 and the central region 24A of the upper wall 24 of the closure part 20 and exposes the central region 43A, leaving the cover part 40 retained on the clamp part 30 by the snap fit lip 43 of skirt wall 42.

FIGS. 1-6 show a relatively small capacity vial 10 of an overall cylindrical profile. For stability and to assist automated handling e.g. during the filling operation and attachment of the cover part 30 the base 10A of the vial 10 is mounted in a ring-shaped stand 50 extending outwardly from the overall cylindrical shape of the vial 10 at its base. The stand 50 has an inner perimeter 51 such that the base of the vial 10 may fit and be retained securely therein, and has an outer perimeter 52 which extends, in a direction perpendicular to the mouth-base axis direction of the vial retained therein 10, beyond the outer diameter of the vial body. The stand 50 has an upward-facing surface 53 and a downward-facing lower 54 surface which are substantially flat and parallel. The vial 10 itself has a base 16 having an upper surface forming the bottom inner surface of the vial 10, and a lower surface from which extends downwardly an integral engagement part 17 able to engage in a tight friction or snap fit with the inner perimeter 51 of the stand 50. It is seen in FIGS. 1 and 3-6 that the outer perimeter 52 of the stand 50 extends radially to substantially the same distance as the radially outermost extent of the clamp part 30.

Figure 1A:
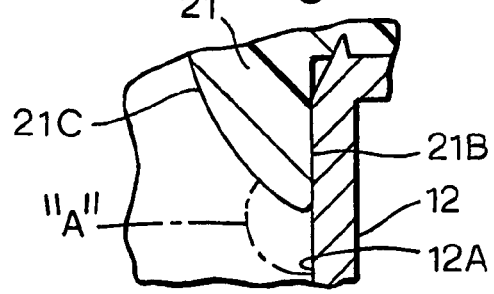

FIG. 1A shows in detail the part of FIG. 1 adjacent to the lower end of the plug part 21 and illustrates a further aspect of this invention in which the plug part 21 has an outward-facing neck-contacting cylindrical surface 21B, which when the closure 21 is in place is against the cylindrical interior surface 12A of the vial neck 12. The closure 21 also has an interior-facing surface 21C which is exposed to the interior of the vial, and which as seen in FIG. 1 when the closure is in place encloses an angle "A" of greater than 90°, being ca. 135°, with the interior surface 12A of the vial neck 12 immediately below the plug part 21.

This angle "A" is achieved by the outward-facing neck-contacting surface 21B of the plug part 21 being generally cylindrical adjacent the lower end of the plug part, and the interior-facing surface 21C and the outward-facing neck-contacting surface 21B forming an edge enclosing an angle of 180° minus A, e.g. ca. 45° between them.

It is found that this profile of the plug part minimises the tendency of surface tension and capillary effects to cause residual liquid content in the vial to become trapped between the closure and the interior surface of the vial. To assist the cylindrical plug part 21 in fitting into the vial neck 12, the vial neck 12 has the slightly conical profile at 12A, being slightly wider at its upper mouth opening than adjacent the lower end of the plug part 21.

The invention claimed is:

1. A closure system for a vial having an upwardly-facing mouth opening bounded by a rim, the closure system comprising:
    an elastomer closure part shaped to sealingly engage with the mouth opening, having a lower surface facing the interior of the vial and an opposite upper surface facing away from the vial, and capable of being punctured by a needle,
    a clamp part able to engage with the vial, and able to bear upon the upper surface of the closure part to hold the closure part in a closing relationship with the mouth opening, the clamp part having an aperture therein through which a region of the upper surface of the closure part is exposed when the clamp part is engaged with the vial, and wherein the clamp part further comprises a peripheral skirt wall extending downwardly and having snap-fit engagement parts thereon to engage the vial via a snap-fit connection, wherein the snap-fit engagement parts are resiliently deformable so that they deform to fit over the rim of the vial and then resiliently snap back to engage the vial via a snap-fit connection,
    a cover part, engageable with the clamp part to cover the said region of the closure part, the cover part at least partly closing the aperture,
    wherein the cover part comprises an upper wall having a segment linked to the remainder of the cover part by a frangible link, said link severable to allow the segment to be sufficiently detached from the remainder of the cover part to thereby allow access to the region of the closure exposed through the aperture and further wherein the cover part comprises a peripheral skirt wall and the skirt wall has a snap-fit engagement part adjacent its lower extremity to engage with the clamp part.

2. A closure system according to claim 1 wherein a lower surface of the segment of the cover part facing the upper surface of the closure part when engaged with the clamp part has a sealing ridge projecting therefrom to a sealing edge that follows a closed perimeter, so that when the cover part is engaged with the clamp part the sealing edge engages with the closure part to form an enclosure with the closure part, the segment which includes the sealing ridge being detachable from the clamp part.

3. A closure system according to claim 1 wherein said frangible link is linked to the skirt wall of the cover part.

4. A closure system according to claim 1 further comprising a downwardly extending plug part which can fit into the mouth opening of the vial, and an outwardly extending peripheral flange part, a downward facing surface of which can engage with the upward facing surface of a rim of the vial mouth opening in the form of a flange, and wherein upwardly of the flange part the closure part is upwardly convex.

5. A closure system according to claim 4 wherein the clamp part comprises:
    an upper wall having the aperture therein, from which the peripheral skirt wall extends downwardly, and
    wherein said upper wall and the upwardly convex part of the closure part are profiled such that the upwardly convex part bulges above the adjacent upper surface of the upper wall.

6. A closure system according to claim 5 wherein said upper surface of the clamp part and the upwardly convex part of the closure part are profiled to form a smooth convex shape.

7. A closure system according to claim 1 wherein the upper surface of the closure part adjacent to the said region is made of a thermoplastic elastomer material.

8. A closure system according to claim 1 characterized in that the clamp part is made of a moldable plastics material and is engageable with the rim bounding the mouth opening of the vial.

9. A pharmaceutical vial having an upwardly facing mouth opening closed by a closure system comprising:
    an elastomer closure part shaped to sealingly engage with the mouth opening, having a lower surface facing the interior of the vial and an opposite upper surface facing away from the vial, and capable of being punctured by a needle,
    a clamp part able to engage with the vial, and able to bear upon the upper surface of the closure part to hold the closure part in a closing relationship with the mouth opening, the clamp part having an aperture therein through which a region of the upper surface of the closure part is exposed when the clamp part is engaged with the vial, and wherein the clamp part further comprises a peripheral skirt wall extending downwardly and having snap-fit engagement parts thereon to engage the vial via a snap-fit connection, wherein the snap-fit engagement parts are resiliently deformable so that they deform to fit over the rim of the vial and then resiliently snap back to engage the vial via a snap-fit connection,
    a cover part, engageable with the clamp part to cover the said region of the closure part, the cover part at least partly closing the aperture,
    wherein the cover part comprises an upper wall having a segment linked to the remainder of the cover part by a frangible link, said link severable to allow the segment to be sufficiently detached from the remainder of the cover part to thereby allow access to the region of the closure exposed through the aperture and further wherein the cover part comprises a peripheral skirt wall, and the skirt wall has a snap-fit engagement part adjacent its lower extremity to engage with the clamp part.

10. A method of closing a vial having an upwardly-facing mouth opening bounded by a rim in the form of a flange having upper and lower surfaces extending transverse to its upper-lower axis, comprising
    inserting into the mouth opening an elastomer closure part shaped to sealingly engage with the mouth opening, and having a lower surface to face the interior of the vial and an opposite upper surface to face away from the vial, and capable of being punctured by a needle,
    providing a clamp part able to engage with the flange around the rim of the mouth opening of the vial by a resilient snap-fit engagement of a snap fit part of the clamp part underneath a downwardly facing surface of such a flange part wherein the snap-fit part is resiliently deformable so that it deforms to fit over the rim of the vial and then resiliently snaps back to engage the flange of the vial via a snap-fit connection, and wherein the clamp part is able to bear upon the upper surface of the closure part to hold the closure part in a closing relationship with the mouth opening, wherein the clamp part further comprises a peripheral skirt wall extending downwardly and having the snap-fit part thereon to engage the vial,
engaging the clamp part with the assembly of vial and closure part by said snap-fit engagement,
providing a cover part comprising an upper wall and a peripheral skirt wall, said cover part being engageable with the clamp part by means of a snap-fit between the clamp part and the skirt wall, wherein when so engaged said cover part covers the closure part and a lower surface of the cover part faces the upper surface of the closure part and
engaging the cover part with the clamp part by said snap-fit.

11. A method of filling a pharmaceutical vial having an upwardly-facing mouth opening, comprising the steps of:
providing an assembly of an empty vial having an elastomer closure part shaped to sealingly engage with the mouth opening and having a lower surface facing the interior of the vial and an opposite upper surface facing away from the vial, and capable of being punctured by a needle, and a clamp part engaged with the vial, and bearing upon the upper surface of the closure part to hold the closure part in a closing relationship with the mouth opening, the clamp part having an aperture therein through which a region of the upper surface of the closure part is exposed when the clamp part is engaged with the vial wherein the clamp part further comprises a peripheral skirt wall extending downwardly and having snap-fit engagement parts thereon to engage the vial;
inserting a filling needle downwardly through the region of the upper wall of the closure part;
injecting a liquid medicament through the filling needle into the vial;
withdrawing the needle to leave a residual puncture hole;
engaging a cover part with the clamp part to cover the said region of the closure part by means of a snap-fit between a peripheral skirt wall of the cover part and the clamp part.

12. A method according to claim 11 further comprising, prior to engaging the said cover part, directing a source of heat at the residual puncture hole in the upper surface of the closure part to melt the elastomer material in the immediate locality of the puncture, and to thereby seal the residual puncture hole.

13. A pharmaceutical vial according to claim 9 retained in a stand, where said stand comprises:
a ring-shaped body having an inner perimeter adapted to engage with the base of the vial; and
an outer perimeter extending radially beyond the outer diameter of the vial body in a direction perpendicular to the mouth-base axis direction of the vial retained therein,
wherein the outer perimeter of the stand extends to substantially the same radial distance as the radially outermost extent of the clamp part when engaged with the vial.

14. A closure system for a vial having an upwardly-facing mouth opening bounded by a rim, the closure system comprising:
an elastomer closure part shaped to sealingly engage with the mouth opening, having a lower surface facing the interior of the vial and an opposite upper surface facing away from the vial, and capable of being punctured by a needle,
a clamp part able to engage with the vial, and able to bear upon the upper surface of the closure part to hold the closure part in a closing relationship with the mouth opening, the clamp part having an aperture therein through which a region of the upper surface of the closure part is exposed when the clamp part is engaged with the vial,
a cover part, engageable with the clamp part to cover the said region of the closure part, the cover part at least partly closing the aperture,
wherein the cover part comprises an upper wall having a segment linked to the remainder of the cover part by a frangible link, said link severable to allow the segment to be sufficiently detached from the remainder of the cover part to thereby allow access to the region of the closure exposed through the aperture and further wherein the cover part comprises a peripheral skirt wall and the skirt wall has a snap-fit engagement part adjacent its lower extremity to engage with the clamp part,
further wherein a lower surface of the segment of the cover part facing the upper surface of the closure part when engaged with the clamp part has a sealing ridge projecting therefrom to a sealing edge that follows a closed perimeter, so that when the cover part is engaged with the clamp part the sealing edge engages with the closure part to form an enclosure with the closure part, the segment which includes the sealing ridge being detachable from the clamp part.

15. A closure system for a vial having an upwardly-facing mouth opening bounded by a rim, the closure system comprising:
an elastomer closure part shaped to sealingly engage with the mouth opening, having a lower surface facing the interior of the vial and an opposite upper surface facing away from the vial, and capable of being punctured by a needle,
a clamp part able to engage with the vial, and able to bear upon the upper surface of the closure part to hold the closure part in a closing relationship with the mouth opening, the clamp part having an aperture therein through which a region of the upper surface of the closure part is exposed when the clamp part is engaged with the vial,
a cover part, engageable with the clamp part to cover the said region of the closure part, the cover part at least partly closing the aperture,
wherein the cover part comprises an upper wall having a segment linked to the remainder of the cover part by a frangible link, said link severable to allow the segment to be sufficiently detached from the remainder of the cover part to thereby allow access to the region of the closure exposed through the aperture and further wherein the cover part comprises a peripheral skirt wall and the skirt wall has a snap-fit engagement part adjacent its lower extremity to engage with the clamp part,
further comprising a downwardly extending plug part which can fit into the mouth opening of the vial, and an outwardly extending peripheral flange part, a downward facing surface of which can engage with the upward facing surface of a rim of the vial mouth opening in the form of a flange, and wherein upwardly of the flange part the closure part is upwardly convex.

16. A pharmaceutical vial retained in a ring stand comprising:
A pharmaceutical vial having an upwardly facing mouth opening closed by a closure system, wherein the closure system comprises an elastomer closure part shaped to sealingly engage with the mouth opening, having a lower surface facing the interior of the vial and an opposite upper surface facing away from the vial, and capable of being punctured by a needle; a clamp part able to engage with the vial, and able to bear upon the upper surface of the closure part to hold the closure part in a closing relationship with the mouth opening, the clamp part having an aperture therein through which a region of the upper surface of the closure part is exposed when the clamp part is engaged with the vial; and a cover part, engageable with the clamp part to cover the said region of the closure part, the cover part at least partly closing the aperture; wherein the cover part comprises an upper wall having a segment linked to the remainder of the cover part by a frangible link, said link severable to allow the segment to be sufficiently detached from the remainder of the cover part to thereby allow access to the region of the closure exposed through the aperture and further wherein the cover part comprises a peripheral skirt wall, and the skirt wall has a snap-fit engagement part adjacent its lower extremity to engage with the clamp part;

wherein the pharmaceutical vial is retained in a stand, where said stand comprises a ring-shaped body having an inner perimeter adapted to engage with the base of the vial and an outer perimeter extending radially beyond the outer diameter of the vial body in a direction perpendicular to the mouth-base axis direction of the vial retained therein, wherein the outer perimeter of the stand extends to substantially the same radial distance as the radially outermost extent of the clamp part when engaged with the vial.

* * * * *